(12) United States Patent
Patton et al.

(10) Patent No.: US 9,597,217 B2
(45) Date of Patent: Mar. 21, 2017

(54) CABLE DRIVEN JOINT ACTUATOR AND METHOD

(71) Applicant: Rehabilitation Institute of Chicago, Chicago, IL (US)

(72) Inventors: James L. Patton, Chicago, IL (US); Michael A. Peshkin, Chicago, IL (US); James S. Sulzer, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 14/597,598

(22) Filed: Jan. 15, 2015

(65) Prior Publication Data

US 2015/0150706 A1 Jun. 4, 2015

Related U.S. Application Data

(62) Division of application No. 11/809,206, filed on May 31, 2007, now abandoned.

(60) Provisional application No. 60/809,698, filed on May 31, 2006.

(51) Int. Cl.
| | |
|---|---|
| B25J 17/00 | (2006.01) |
| A61F 5/01 | (2006.01) |
| A61H 1/02 | (2006.01) |
| A63B 21/00 | (2006.01) |
| F16H 19/06 | (2006.01) |
| A61H 3/00 | (2006.01) |
| A63B 21/005 | (2006.01) |

(52) U.S. Cl.
CPC .......... *A61F 5/0102* (2013.01); *A61F 5/0125* (2013.01); *A61H 1/0237* (2013.01); *A61H 1/0274* (2013.01); *A61H 3/00* (2013.01); *A63B 21/155* (2013.01); *F16H 19/06* (2013.01); *A61H 2201/1215* (2013.01); *A61H 2201/163* (2013.01); *A61H 2201/165* (2013.01); *A61H 2201/1635* (2013.01); *A61H 2201/1642* (2013.01); *A61H 2201/1676* (2013.01); *A63B 21/0058* (2013.01); *A63B 2220/17* (2013.01); *A63B 2220/51* (2013.01); *Y10T 74/20402* (2015.01)

(58) Field of Classification Search
CPC ... A61F 5/0106; A61F 5/0125; A61H 1/0237; A61H 3/00; F16H 19/06
USPC ...................................... 74/490.04
See application file for complete search history.

(56) References Cited

U.S. PATENT DOCUMENTS

| | | |
|---|---|---|
| 3,142,459 A | 7/1964 | Baetke |
| 3,448,633 A | 6/1969 | Jackoboice |
| 4,067,070 A | 1/1978 | Seamone et al. |
| 4,433,679 A * | 2/1984 | Mauldin ............... A61F 5/0125 602/16 |
| 4,784,010 A | 11/1988 | Wood et al. |
| 5,163,340 A | 11/1992 | Bender |
| 5,207,114 A | 5/1993 | Salisbury et al. |
| 5,549,712 A | 8/1996 | Gammer et al. |
| 5,873,734 A | 2/1999 | Griswold et al. |

(Continued)

*Primary Examiner* — Vicky Johnson
(74) *Attorney, Agent, or Firm* — Polsinelli PC; Ari M. Bai

(57) ABSTRACT

A cable driven actuator and actuator method involve a movable link that is movable about a path by a cable connected to the link, and a movable support member having a cable routing element. The support member is movable in a manner to change a moment arm of the cable acting on the link to control torque applied to the joint.

18 Claims, 6 Drawing Sheets

(56) References Cited

U.S. PATENT DOCUMENTS

| | | | | |
|---|---|---|---|---|
| 5,888,235 A | * | 3/1999 | Jacobsen | A61F 2/54 |
| | | | | 623/58 |
| 7,278,954 B2 | * | 10/2007 | Kawai | A61H 3/00 |
| | | | | 482/1 |
| 7,731,673 B2 | * | 6/2010 | Hiki | A61H 1/0237 |
| | | | | 602/16 |
| 2004/0106881 A1 | * | 6/2004 | McBean | A61B 5/04888 |
| | | | | 601/5 |
| 2004/0250644 A1 | | 12/2004 | Gosselin et al. | |

* cited by examiner

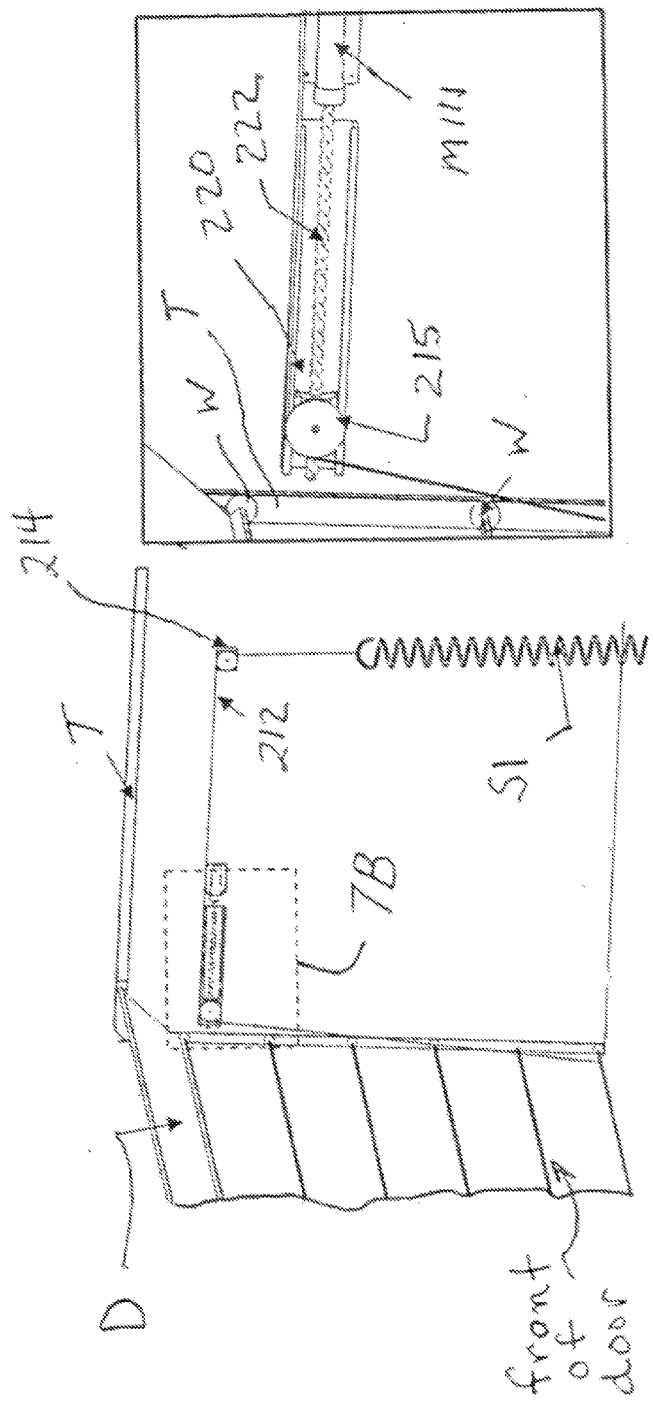

CABLE DRIVEN JOINT ACTUATOR AND METHOD

CROSS REFERENCE TO RELATED APPLICATIONS

This is a divisional application that claims benefit to U.S. non-provisional application Ser. No. 11/809,206 filed on May 31, 2007, which claims benefit to U.S. provisional application Ser. No. 60/809,698 filed on May 31, 2006, which are herein incorporated by reference in their entirety.

GOVERNMENT SUPPORT

This invention was supported by funding from the Federal Government through the National Institute of Health Science under Grant/Contract No. 5T32 HD 07418. The Government may have certain rights in the invention.

FIELD

The present invention relates to a cable driven actuator and method incorporating moment arm adjustment features.

BACKGROUND

In rehabilitation robotic, orthotic, or prosthetic applications, devices have been used to apply forces including torques to various points on the human body in order to manipulate those points. When such devices apply forces or torques under programmable computer control, it is said that the human body is subject to robotic manipulation.

Current robotic manipulation can be used to provide benefits to clinicians and patients that include, but are not limited to, assessment, motor control studies, and therapy of both healthy people and people with neuromuscular difficulties. However, the robotic machines developed to date have been limited for use in a laboratory setting.

A robotic machine capable of training or rehabilitating its human user at home or otherwise outside of a laboratory has the potential to be used more often and thus be more effective. Such a robotic machine should be lightweight, inexpensive, and portable, which current rehabilitation robotic machines cannot offer.

Rehabilitation robotic devices known as the STRING-MAN device (Surdilovic et al. "STRING-MAN: A New Wire Robotic System For Gait Rehabilitation", Proc. 8$^{th}$ International Conference on Rehabilitation Robotics, 2003) and MACARM device (Mayhew et al. "Development of the MACARM—a Novel Cable Robot for Upper Limb Neurorehabilitation". Proceedings of the 2005 IEEE, 9$^{th}$ International Conference on Rehabilitation Robotics, Chicago, Ill. 2005) use cables to actuate a human user's joints. The torque on the human user's joint is controlled by changing the tension in the wires.

The MIT Manus device uses a five-bar linkage and two torque motors to produce a planar haptic interface (Hogan et al. "MIT-MANUS: a workstation for manual therapy and training", IEEE International Workshop on Robot and Human Communication", pp. 161-165, Tokyo, Japan 1992). As a linkage, where the individual bars are of fixed length, motion pathways are prescribed by the motions of the joints and by design and size of the linkage.

Several human interactive robots have embodied Bowden cables guided by pulleys or drums. For example, such a robot is described by Jacobsen et al. in "Design of the Utah/MIT Dextrous Hand", Proc. IEEE International Conference on Robotics and Automation (ICRA), San Francisco 1986. Also see Salisbury et al. "The Design and Control of an Experimental Whole-Arm Manipulator", Proc. 5$^{th}$ Int. Symp On Robotics Research 1989; and Perry et al. "Design of a 7-Degree-of-Freedom Upper-Limb Powered Exoskeleton", Proc. Int. Conf. of Biomedical Robotics and Biomechatronics, Pisa, Italy 2006.

A robotic actuator for dynamic legged locomotion using a cable-driven series elastic actuator is described by Hurst et al. in "An Actuator with Physically Variable Stiffness for Highly Dynamic Legged Locomotion", International Conference on Robotics and Automation, New Orleans 2004). Also see Veneman et al. "Design of a Series Elastic and Bowden cable-based actuation system for use as torque-actuator in exoskeleton-type training", International Conference on Rehabilitation Robotics, Chicago, Ill. 2005).

A robotic machine that embodies two elastic bands connected to a passive (non-driven) circular disk and that relies on torque unbalance to cause the passive disk to jump between positions is described by Zeeman in "Catastrophe Theory: Selected Papers", Addison-Wesley 1972-1977.

SUMMARY OF THE INVENTION

The present invention provides a cable driven actuator mechanism that includes moment arm adjustment features to manipulate the position of the moment arm relative to a movable link.

In an illustrative embodiment of the present invention, a cable driven joint actuator includes a movable link that can be operatively coupled to a joint to be actuated and that is movable about a path by a cable connected to the link. A cable routing element is provided on a movable support member that is rotated and/or translated in a manner to change the moment arm of the cable acting on the link to control torque applied to the joint. The joint can include but is not limited to, a human user's joint or a mechanical joint of a mechanical device.

In a particular illustrative embodiment of the present invention, the cable driven joint actuator includes a pivotal link that is adapted to be operatively coupled to a joint to be actuated and that is pivoted about a pivot axis by a length of cable engaging a pulley on the link remote from the pivot axis and having an end coupled to the link. One or more cable positioning pulleys is/are provided on a rotatable pulley-support member that is rotated about an axis that is coaxial with the pivot axis to cause the cable positioning pulley to reposition the cable in a manner to change the moment arm of the cable acting on the link to control torque applied to the joint. The rotatable pulley support member is rotatable by a first motor. A device is provided to maintain a substantially constant tension on the cable. The device can comprise a cable spool and a second motor to rotate the spool. The pulley on the link and the cable positioning pulley on the movable pulley-support member can be configured as a block and tackle to amplify torque applied to the joint.

The present invention is useful as a robotic training or rehabilitating machine, prosthetic machine, or orthotic machine for human patient use at home or otherwise outside of a laboratory as a result of its being lightweight, inexpensive, and portable.

The present invention envisions a cable driven actuator for a human limb comprising a cable connected to a human limb that comprises a pivotal link to be actuated and that is pivoted about an axis by the cable, the cable being connected to the human limb remote from the axis. A movable support member includes a cable routing element wherein the support member is movable in a manner to change a moment arm of the cable acting on the human limb to control torque applied about the joint.

The present invention envisions a cable driven actuator for a garage door or other mechanical link wherein the position of the moment arm relative to a mechanical link is manipulated.

These and other features and advantages of the present invention will be set forth in the following detailed description taken with the following drawings.

DESCRIPTION OF THE DRAWINGS

FIGS. 7A and 7B are schematic views of a garage door opener mechanism in "door going up" position, where the moment arm in the cable is set to lift the door up.

DESCRIPTION OF THE INVENTION

In one illustrative embodiment, the present invention provides a cable driven joint actuator mechanism that includes moment arm adjustment features to control torque applied to a joint. The joint to be actuated can include, but is not limited to, a human user's joint such as an elbow joint, a mechanical joint of a mechanical device, or any other joint.

Figure 1:
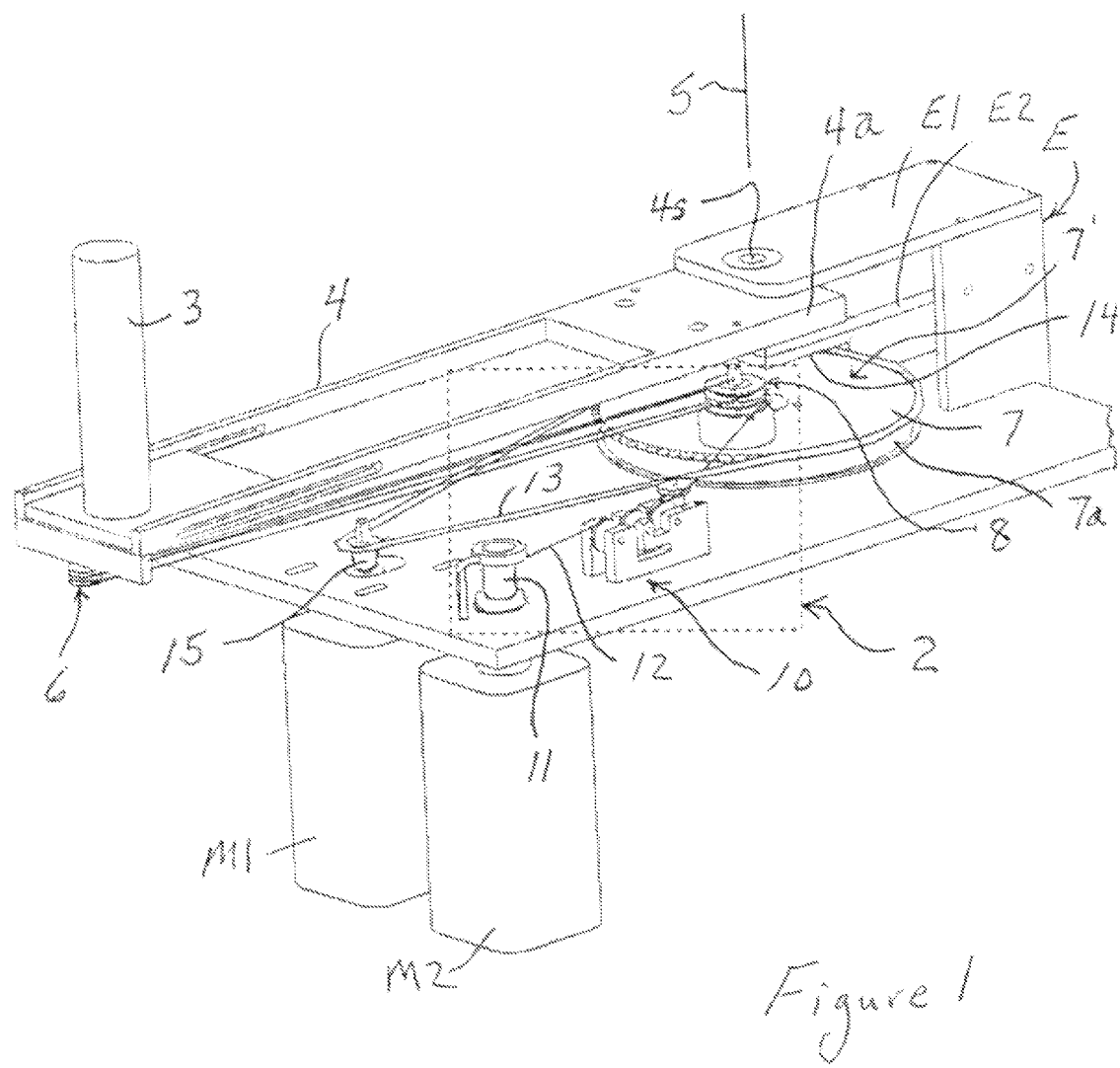
FIG. 1 is perspective view of a cable driven joint actuator in accordance with an illustrative embodiment of the invention.
Figure 2:
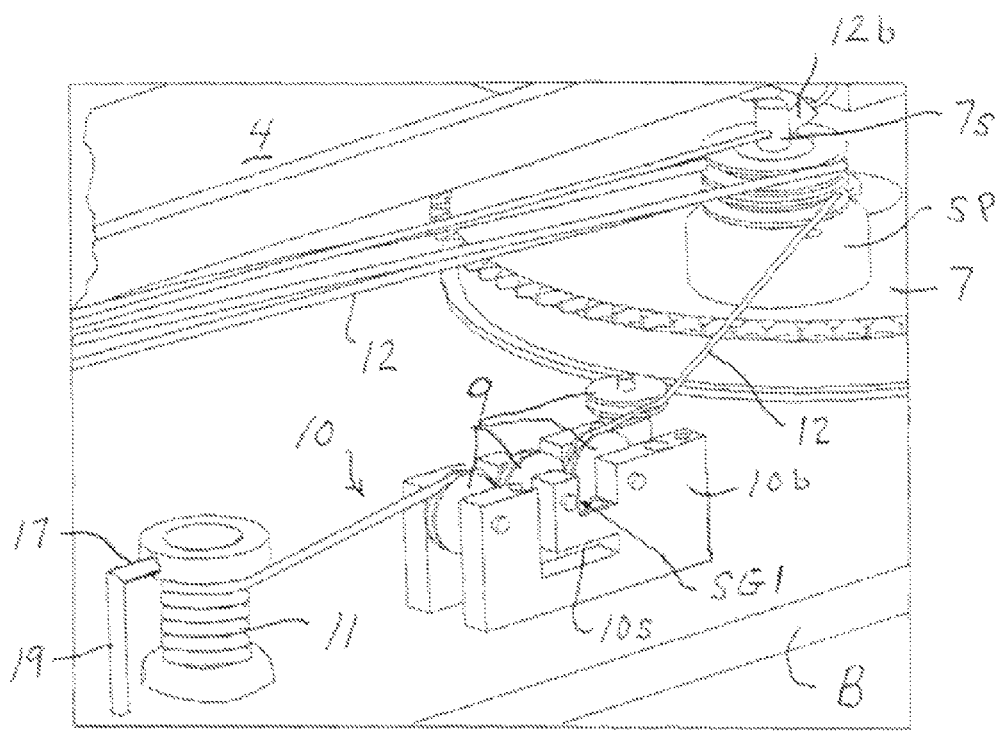
FIG. 2 is an enlarged perspective view of the rotator and the cable tensioner of the cable driven joint actuator of FIG. 1.
Figure 3:
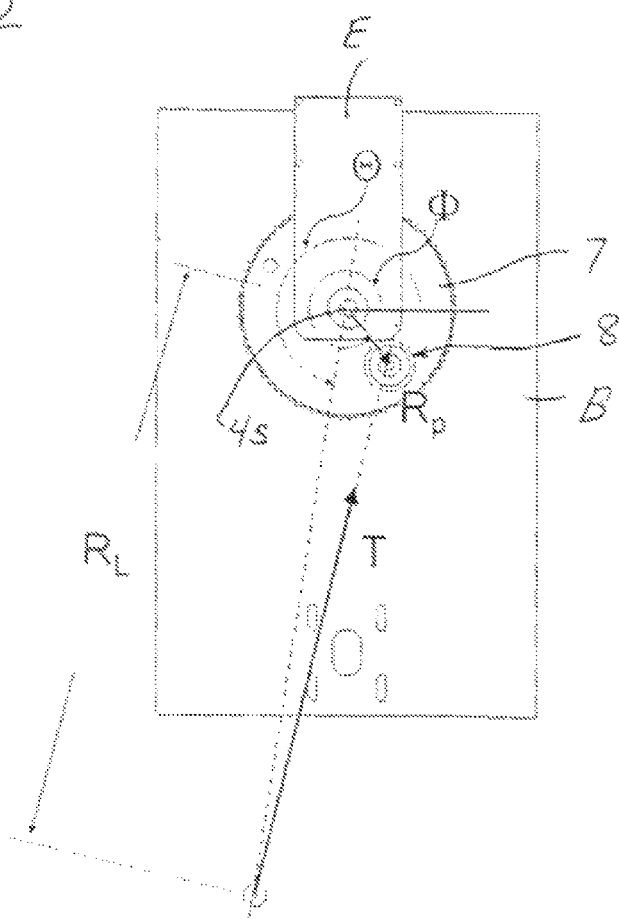
FIG. 3 is a simplified top view meant to show the variables involved in calculating torque exerted in the joint.

In a particular embodiment of the present invention offered for purposes of illustration and not limitation with respect to FIGS. 1 and 2, the cable driven joint actuator includes a pivotal link 4 that is adapted to be operatively coupled to a joint to be actuated and that is pivoted about a pivot axis 5 by a discrete length of substantially inelastic cable 12 engaging one or more pulleys 6 disposed on the link 4 remote from the pivot axis 5 and having a cable end coupled to the link as explained below. One or more cable positioning pulleys 8 is/are provided on a rotatable pulley-support member 7 that is rotated about a center axis that is coaxial with the pivot axis 5 to cause the one or more cable positioning pulleys 8 to position the cable in a manner to change the moment arm of the cable acting on the link to control torque applied to the joint. Moment arm is defined using geometry from FIG. 3. The angle of the cable positioning pulleys 8 relative to a datum, φ, and the angle of the pulleys of link 4 relative to the same datum, θ, are combined with the radius of the link 4 and the cable positioning pulleys 8, $R_L$ and $R_P$, respectively. The equation for the moment arm, R, is shown below:

$$R = \frac{R_L R_P}{\sqrt{R_L^2 + R_P^2 - 2R_L R_P \cos(\Theta - \Phi)}} \sin(\Theta - \Phi).$$

The rotatable pulley support member 7 is rotatable by a first motor M1. A cable tensioner device 10 is provided to maintain a substantially constant tension on the cable 12. The tensioner device 10 can comprise a cable spool 11 and a second motor M2 to rotate the spool 11. In FIGS. 1 and 2, two cable pulleys 6 are shown disposed on the link 4 and two cable pulleys 8 are shown disposed on the pulley-support member 7 configured to form a block and tackle to amplify torque applied to the joint. The various components of the actuator are disposed on a base plate B having a base plate frame E. The end 4a of the link 4 is rotatably mounted between the frame plates E1, E2 of the frame E.

A particular illustrative working embodiment of the invention is now described in more detail with respect to FIGS. 1 and 2. The link 4 rotates about the pivot axis 5 defined by a link pivot shaft 4s sandwiched between two ½ inch inner diameter ABEC 1 bearings from McMaster-Carr Supply Company and mounted between the frame plates E1, E2. The angular position θ of the link 4 is measured by a 10 KΩ conductive plastic potentiometer 14 from Spectrum Sensors and Controls, Inc. with a resolution of 0.03°. (0.0005 radians). The potentiometer is rotated by the rotatable link shaft 4s that rotates about axis 5.

An adjustable handle 3 is provided and can slide across a track on the link 4 to fit a variety of user arm lengths. Two link pulleys 6 are shown located at the remote end of the link 4 so as to form the distal portion of the cable block and tackle. The pulleys 6 comprise ⅝ inch outer diameter pulleys from McMaster-Carr Supply Company and are mounted atop one another on the link by a 3/16 inch diameter steel shaft. All machined components (except for steel shafts) are made of 6061 aluminum alloy.

The pulley-support member 7 comprises a six inch pitch diameter, steel sprocket (Stock Drive Products, Sterling Instrument, 0.25 inch pitch) rotating about its center axis that is coaxial with pivot axis 5 and a roller chain 13 (0.25 inch pitch). The sprocket is rigidly connected to a support hub 7a to prevent wobbling of the sprocket. The member 7 and hub 7a are rotatably mounted on two 0.5 inch inner diameter ABEC 1 bearings from McMaster-Carr Supply Company on a steel shaft 7s fixed to ground (i.e. base plate B). The shaft 4s and the shaft 7s have the same center of rotation. The pulleys 8 (both ⅝ inch outer diameter) are positioned by a spacer SP to be roughly at the same height as the link 4 for efficient cable-wrapping. Each pulley 8 uses a ¼ inch inner diameter ABEC 1 bearing from McMaster-Carr Supply Company. The pulleys 8 are fastened in a fixed position on the member 7 (1.9375 inches from the sprocket center) on fixed shaft 7s. The angular position φ of the pulleys 6 is measured by the drive motor M1 with an encoder described below. The larger rotating member (sprocket) 7 and the pulleys 8 disposed thereon for rotation are known together as the rotator 7'.

The rotator 7' is driven by a roller chain 13 and sprocket 15 from Stock Drive Products, Sterling Instrument having a 0.25 inch pitch, 0.6 inch pitch diameter coupled to a drive motor M1, which comprises a Yaskawa AC servomotor (SGM-02B312) with 0.637 Nm continuous torque. The sprocket drive motor M1 is provided with an encoder with 8192 counts/revolution that is used as feedback to measure pulley angle φ. Through the transmission ratio of 10, the resulting resolution of the position is 0.016.degree. (0.0003 radian). The transmission ratio of 10 results from the ratio of the drive motor coupler (not shown of 0.6 inch diameter) to the sprocket (6 inch diameter). Consistent with cable design principles, the angle of incidence of the cable (the fleet angle) does not exceed 2°, the cable does not reverse wrapping, and the pulleys are above the minimum diameter as described by Oberg et al., Machinery's Handbook, 26$^{th}$ Edition: Industrial Press Inc. which is incorporated herein by reference to this end.

The rotator 7' and the link 4 are mechanically coupled by a steel aircraft cable 12 from Sava Industries (1/32 inch diameter, 7×19 strands) that wraps around the rotator pulleys 8 and the link pulleys 6 in a block and tackle configuration to amplify the effective tension of the cable by four, resulting in a four-fold increase in torque and cable excursion. The path of wrapping of the cable from the tensioner device 10 passes through the bottom pulley of the cable positioning pulleys 8, then through the bottom pulley of the link pulleys 6, back to the top pulley of the cable positioning pulleys 8, and then back to the top pulley of the link pulleys 6 until it is anchored back at the shaft 7s of the cable positioning pulleys 8 by anchor 12b. To account for the increased excursion, cable tensioner device 10 is provided on the base plate B and comprises a spool 11 driven by a tensioner motor M2, which is also a Yaskawa AC servomotor (SGM-02B312) for multiple cable wraps. The cable 12 wraps around the spool 11 which couples to the tensioner motor M2 with a resolution of 0.16 N, which includes the transmission ratio. Since the cable 12 enters the spool at a large fleet angle but a small fleet angle is desired for better wrapping, a device that decreases the fleet angle at any wrapping level is necessary. This embodiment uses a follower 17 with the same pitch and thread diameter that guides the cable into the spool 11. Since the follower needs to rise and fall with the level of cable on the spool yet maintain consistent orientation, a post 19 is provided with one end fixed to the follower and the other end translatable vertically in the base plate B. The follower 17 is similar to a follower employed on a fishing reel. Proximate one end, the cable 12 runs against the follower 17 and wraps up to the spool 11 as it rotates. Exiting from the follower, the cable needs to match up to the height of the rotator's pulleys 8. As a result, the cable 12 travels through a cable guidance system that comprises of four pulleys 9 provided to both raise the cable to the proper constant height when approaching the rotator pulleys 8 and also to measure cable tension. The pulleys 9 comprise ½ inch diameter pulleys from McMaster-Carr Supply Company disposed on fixed support block 10b. There are provided two strain gauges (strain gauge SG 1 being shown on block 10b and the other strain gauge being located therebelow on the underlying block surface 10s) that are disposed on the pulley support block 10b in a manner to detect cable tension and provide an optional feedback loop with the tensioner motor M2. The strain gauges can comprise 350 Ω. resistance strain gauges SG from Omega Engineering, Inc. Cables for use in practice of the invention can include, but are not limited to, steel aircraft cable or other substantially inelastic cables. Elastic cables can be used as well such as one or more bungee cords within the scope of the invention. As used herein, the term cable or cables is intended to include a cable, cord, strand, rope, belt, or other substantially inelastic or flexible, elastic elements.

In lieu of the cable being connected to the tensioner device 10 as described above, the cable can be connected to a source of energy storage such as including, but not limited to, a spring, FIG. 7A, 7B, or even an energy dissipation element, such as a damper and bungee cord.

From the above description, it is evident that the drive motor M1 controls the rotational path of the cable positioning pulleys 8 such that the rotator 7' is driven remotely, and the other tensioner motor M2 controls the tension in the cable 12. Moreover, the rotator (disk 7 with pulleys 8) and the link 4 rotate independently from one another, coupled only by the cable 12.

An advantage of the cable driven joint actuator described above is its simple control strategy. Using a real time operating system, the data comprised of the angular positions of the link 4 and of the rotator 7' (disk 7 with pulleys 8) are sampled at 2 kHz. The drive motor M1 which controls the rotator 7' is operated in a torque mode, using encoder feedback and controls position. The tensioner motor M2 is operated in open loop torque mode when the strain gages SG 1, etc. are not used, where a voltage command determines the desired tension in the cable. A general-purpose, procedural, imperative computer programming language, such as C++, and that interrupts in a semaphore structure to control the actuator motors M1 and M2 of FIGS. 1, 2, and 3.

The desired torque to be applied to a joint is created by setting the position of rotator 7' to create the proper relative angle between itself and the link 4. For example, the torque per unit tension is the derivative of the excursion according to the position of the link 4 pursuant to: The torque on the arm is the product of the moment arm and the effective tension, which through the block and tackle, is four times the tension:

$$\overline{T} = R \cdot 4T$$

where $\overline{T}$ is torque, T is tension in the cable, R is the moment arm defined above. Endpoint stiffness can be manipulated in the same manner. It is noted that changing the rotator position is equivalent to changing the equilibrium position of the actuator. The link position (determined from the potentiometer) and the rotator position (determined from the motor encoder) are the only feedback components necessary for control of the actuator, since the tension of the cable 12 is held constant in this particular working embodiment. Hard mechanical stops (not shown) are provided to prevent the link 4 from surpassing the user's range of motion. A chain guard (also not shown) can be provided to cover the exposed portion of the roller chain 13 to prevent any interference.

Figure 4:
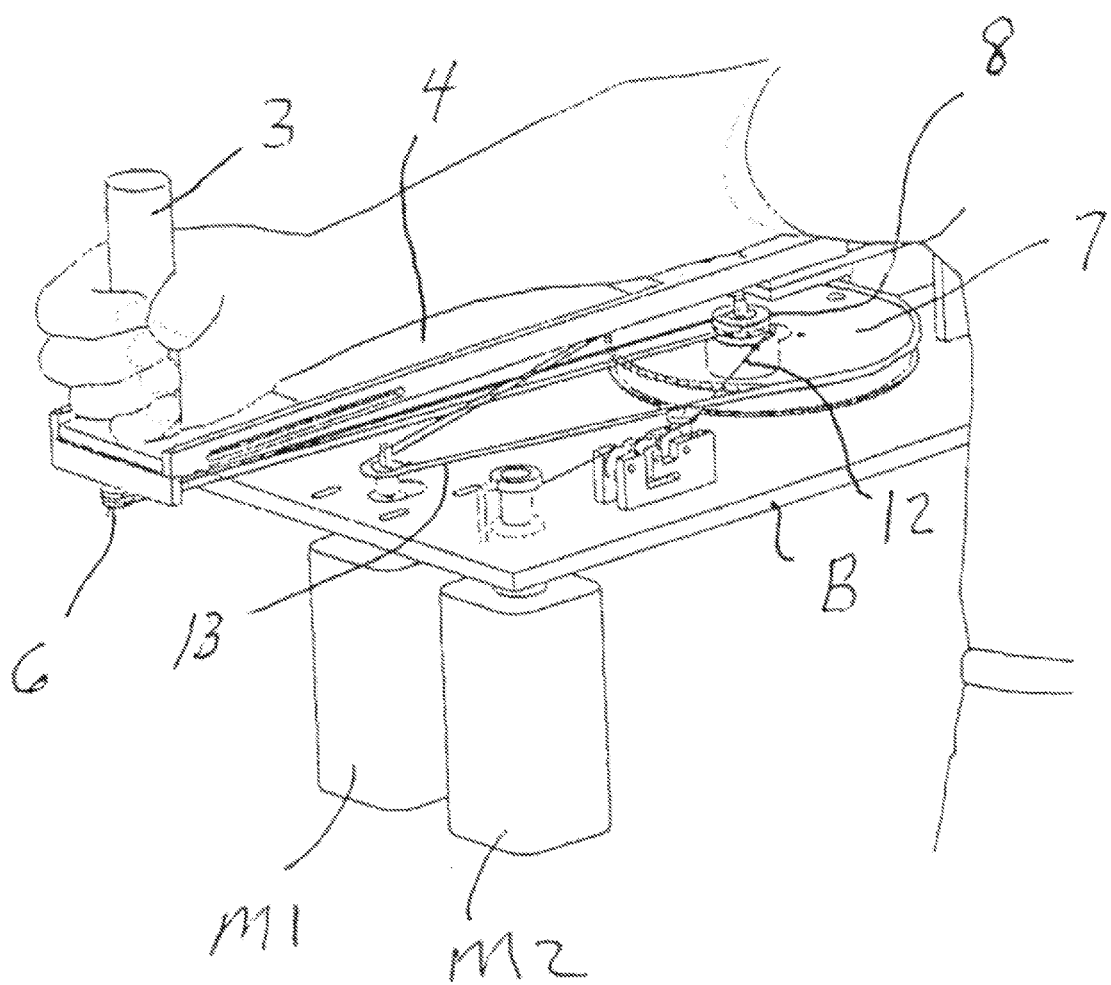
FIG. 4 is a schematic view of a human user grasping the handle for use in training or rehabilitation where the actuator applies a torque about the elbow joint.

The cable driven joint actuator described above can be used in an illustrative embodiment as a robotic training or rehabilitating machine, FIG. 4, for a human user who grasps the handle 3 on the link 4 so that torque is applied by the actuator about the elbow joint of the user, centered at the pivot point 5. The Table below shows illustrative design parameters for such use. In the Table, the user's forearm length refers to an actual user's forearm, on which the length of the link 4 is sized and adjusted, if necessary.

TABLE

Quantitative Design Parameters

| | Range of Motion from full extension (rad) | User Forearm Length (m) | Torque (N · m) | Speed (rad/s) |
| --- | --- | --- | --- | --- |
| Minimum | 0 | 0.28 | 0 | 0 |
| Maximum | 3π/4 | 0.4 | 10 | 50 |

The above range of torques is based on a 25 N endpoint force, and the maximum speed is based on an 8 Hz movement. The training or rehabilitating machine can be used in various modes of operation; for example, in a Guidance mode where the actuator torque pushes the user's arm/hand about the elbow joint toward the desired trajectory of movement using a linear force field of 8 Nm/radian; in an Error Augmentation mode where the actuator torque pushes the user's arm/hand about the elbow joint away from the desired trajectory of movement using a linear force field of 8 N m/radian; and in a Control mode where there is no haptic feedback (actuator motor M1 not energized). In summary, the device can be used to control either position or exert any accurate torque on its user as long as the bandwidth and maximum torque are within specifications.

In lieu of using the rotator 7' described above to manipulate the moment arm, the invention envisions using a slide or compound slide (not shown) having one or more cable positioning pulleys disposed thereof to engage and position the cable. The slide or compound slide can be moved linearly by a motor of any type in a direction to manipulate the moment arm. In fact, the invention envisions manipulating the moment arm in any given path, whether it be linear, rotational, or a combination of the two.

Figures 5A, 5B:
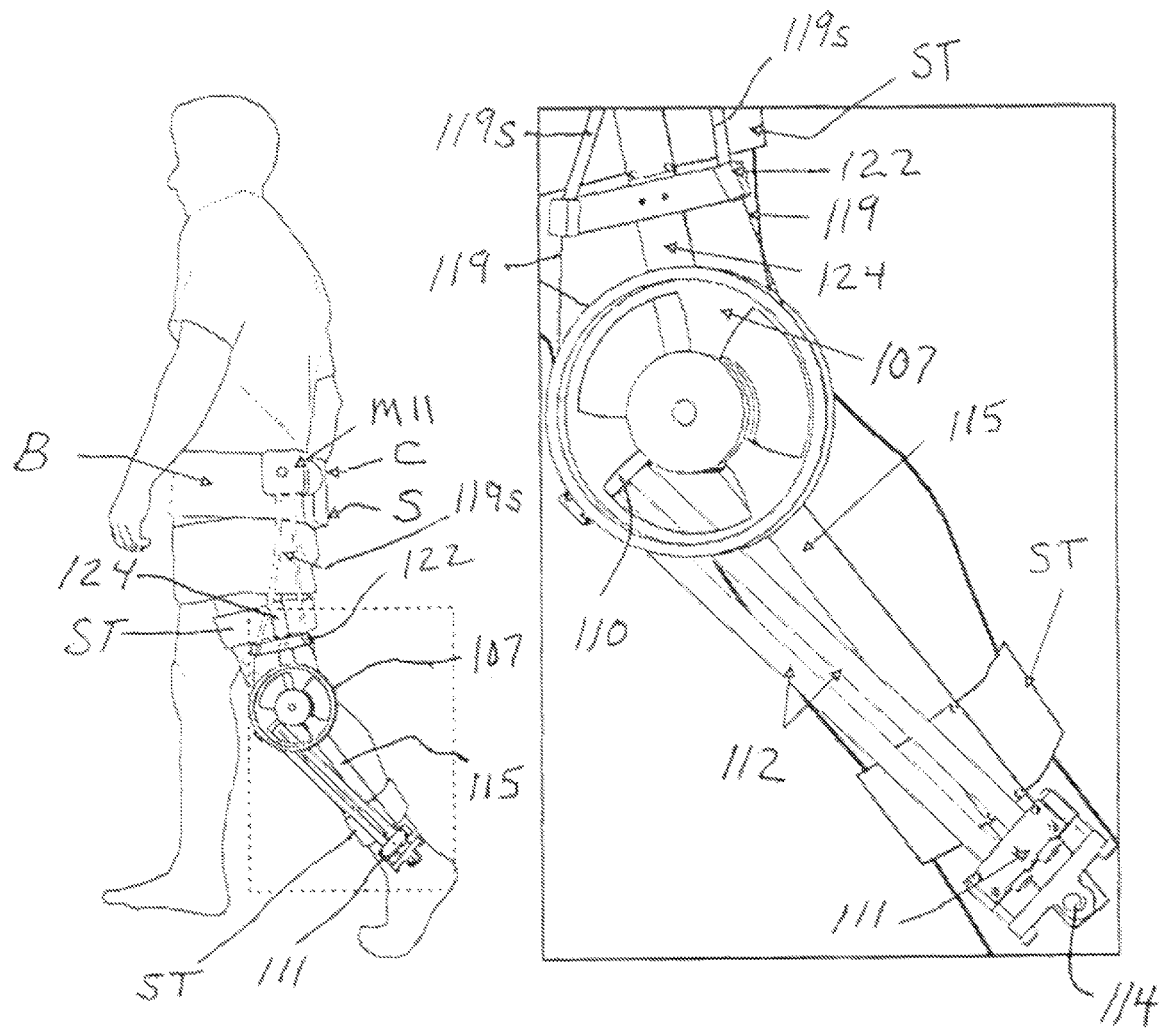
FIG. 5A is a schematic view of a human user having a cable driven actuator to apply torque about the knee joint to move the user's leg.
FIG. 5B is an enlarged view of the region boxed-in by dashed lines in FIG. 5A.
Figure 6:
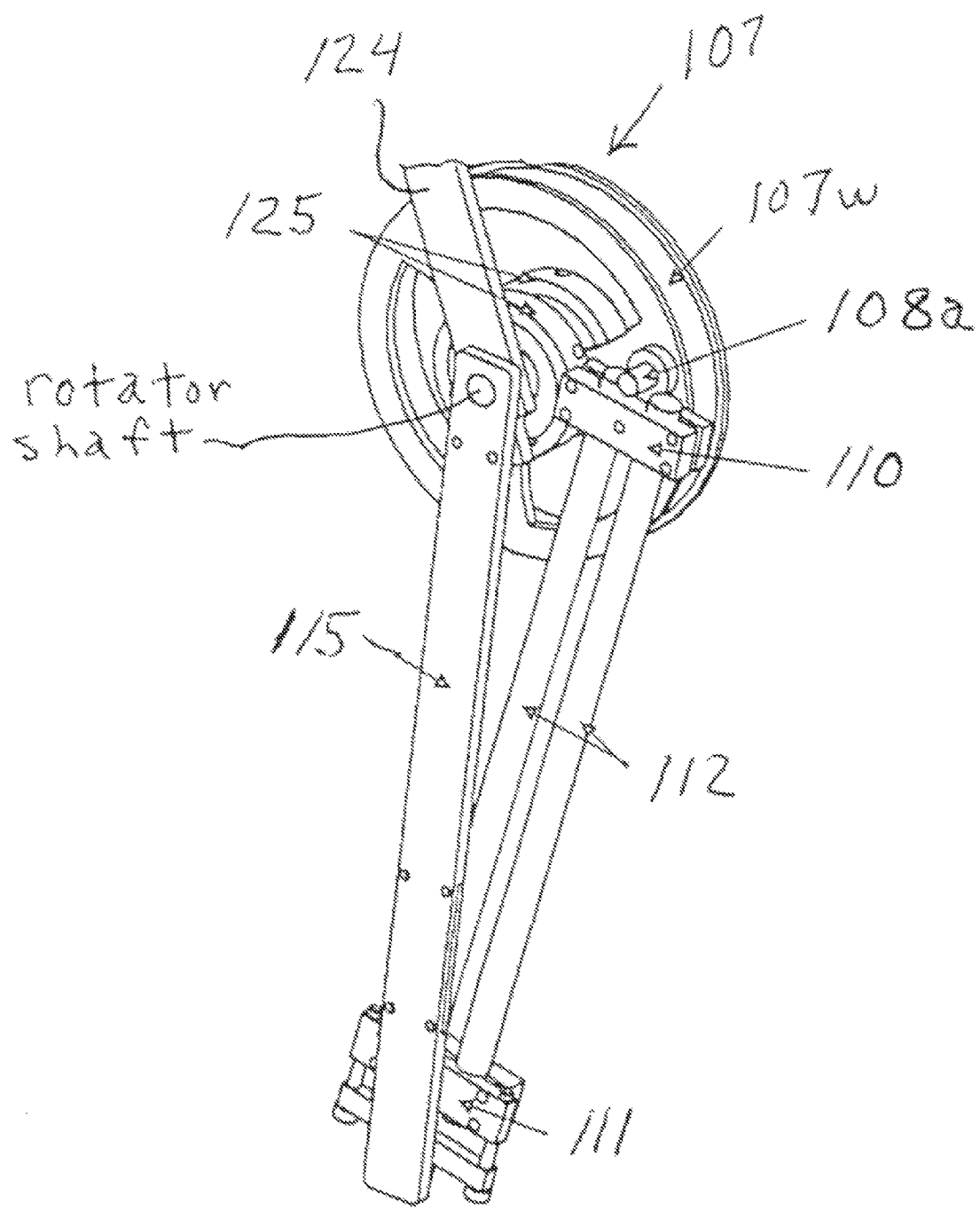
FIG. 6 is a view of the opposite side of the knee orthosis.

FIGS. 5A, 5B and 6 are schematic views of a human user having a cable driven actuator to apply torque about the knee joint in a manner to move the user's leg pursuant to another illustrative embodiment of the invention. The cable driven actuator is attached by straps ST to the leg of the user. FIG. 6 provides a view of the device from the opposite side. FIG. 6 shows a rotator 107 having cable wrapping surface 107w and having a fixed shaft 108a that is connected to a proximal bungee cord anchor 110 which fixes the ends of two bungee cords 112 and that allows the anchor 110 to rotate about the shaft 108a. In this embodiment, the cable routing element is the proximal bungee cord anchor 110. The other ends of the bungee cords are fixed in a distal bungee cord anchor 111 that connects to a fixed shaft 114 distally located on a rigid leg support member 115 in a manner that allows the anchor 111 to rotate about the shaft. The rotator 107 is centered at the knee, and moves in a rotational manner about its rotator shaft, thus moving the proximal bungee cord anchor 110 in a rotational manner.

The position of the rotator 107 is controlled by cable 119 that wraps around the rotator surface 107w and then passes through sheaths 119s to a motor M11 on a belt B donned by the user. One end of each cable sheath 119s is anchored to an anchor plate 122 of a rigid thigh support member 124 and referred to as a Bowden sheath anchor. The other end of each sheath 1119s is rigidly connected to the motor M 11 which wraps the other end of the cable. The members 115, 124 relatively rotate about the rotator shaft during leg movement. The user's belt B also can include a controller C and power source S, such as a battery pack The rotational path of the proximal bungee anchor 110 varies both the length of the bungee cord and the moment arm, altering the torque exerted on the knee. There are two angular position sensors (goniometers) 125 that detect the position of both the rotator 107 and the leg relative to the thigh. Since the torque varies based on rotator position relative to knee flexion angle, the position of the rotator can be varied relative to the leg, and thus a controlled torque can be provided at the knee. The torque could be used for any number of embodiments, including assistive and resistive strategies.

In another illustrative embodiment of the present invention, a cable driven actuator mechanism is provided that includes moment arm adjustment features to manipulate the position of the moment arm relative to a movable link. For purposes of illustration and not limitation, FIGS. 7A and 7B show a cable driven joint actuator according to this embodiment for use as a garage door opener device. In this embodiment, an inelastic cable 212 attached on one end to an extension spring S1 fixed to ground, passes through a fixed pulley 214 and then through another pulley 215 attached to a linearly movable bearing 220 for linear movement therewith. The pulley 215 comprises a cable routing element. The linearly movable bearing 220 provides a movable support member for the cable positioning pulley 215. The bearing 220 is moved in linear manner by lead screw 222 driven by motor M111. The cable 212 then attaches to the bottom of a conventional multi-hinged garage door D. The garage door has wheels W that rotate around each hinge and travel along a fixed track T, which provides a path for movement of the garage door. The garage door itself or the door sections is considered a movable link.

The device works by manipulating the moment arm of the cable 212 relative to the position of the door D. To open a closed door, motor M111 moves the linear bearing 220 (with cable positioning pulley 215 thereon) along a horizontal path towards the door, modifying the cable's line of action it creates with the door and thus the spring tension in the cable in the vertical direction is larger than the weight of the door causing the door to rise. To close an open door, the motor M111 will move the linear bearing 220 (with cable positioning pulley 215 thereon) away from the door until the weight of the door is greater than the vertical direction of the tension in the cable.

While certain embodiments of the invention have been described in detail above, those skilled in the art will appreciate that changes and modifications can be made therein within the scope of the invention as set forth in the appended claims.

What is claimed is:
1. A cable driven actuator comprising:
 a rotator defining a central axis and a wrapping surface,
 a cable engaged to the wrapping surface of the rotator,
 a motor operatively connected to the cable to cause rotation of the rotator about the central axis when the cable is driven by the motor;
 a first shaft disposed on the rotator and extending outwardly from the rotator and located a predetermined distance from the central axis of the rotator;
 a support member defining an elongated body having a first end and a second end, the first end of the support member being engaged to the central axis to permit rotation of the first end relative to the central axis of the rotator; and
 a tensioning arrangement having a first end and a second end, the first end of the tensioning arrangement being coupled to a proximal anchor that rotates about the first shaft of the rotator and the second end of the tensioning arrangement being coupled to a distal anchor that rotates about a second shaft that extends from the second end of the support member.

2. An orthosis comprising the cable driven actuator of claim 1.

3. The orthosis of claim 2, further comprising the motor for causing rotation of the rotator about the central axis.

4. The system of claim 3, further comprising:
 a controller for controlling the strategy of the actuator and
 a power source for powering the motor.

5. The system of claim 4, wherein at least one of the controller and the power source is configured to be worn on a belt.

6. The system of claim 4, wherein the controller is programmed for an assistive strategy that provides assistance to the user of the system.

7. The system of claim 4, wherein the controller is programmed for a resistive strategy that provides resistance to the user of the system.

8. An orthosis comprising the system of claim 7.

9. The system of claim 4, wherein controller is configured to adjust a torque applied to the actuator by the motor, on the basis of the position of the rotator and a position of a limb of the user.

10. An orthosis comprising the system of claim 9.

11. An orthosis comprising the system of claim 4.

12. The orthosis of claim 2, further comprising a thigh strap and an ankle strap.

13. The orthosis of claim 2, wherein the rotator has a first orientation in which the rotator is positioned adjacent to a knee joint.

14. The orthosis of claim 2, wherein in the first orientation, the central axis of the rotator is co-linear with an axis of rotation of the knee joint.

15. The orthosis of claim 2, wherein in the first orientation, the first shaft disposed on the rotator extends outwardly from the rotator and towards the knee joint.

16. The orthosis of claim 2, wherein the rotator further comprises a hub and a plurality of spokes, the spokes connecting the hub to the wrapping surface of the rotator.

17. The orthosis of claim 2, further comprising a wearable belt, wherein the motor is positioned on the belt.

18. The cable driven actuator of claim 1, wherein the tensioning arrangement comprises a bungee cord.

\* \* \* \* \*